United States Patent [19]

Sasaki et al.

[11] Patent Number: 4,992,350

[45] Date of Patent: Feb. 12, 1991

[54] BIPHENYL COMPOUNDS AND ELECTROPHOTOGRAPHIC PHOTOCONDUCTOR COMPRISING THE SAME

[75] Inventors: Masaomi Sasaki, Susono; Tamotsu Aruga, Mishima; Tomoyuki Shimada, Numazu, all of Japan

[73] Assignee: Ricoh Company, Ltd., Tokyo, Japan

[21] Appl. No.: 409,421

[22] Filed: Sep. 19, 1989

[30] Foreign Application Priority Data

Sep. 30, 1988 [JP] Japan ............................ 63-247037
Sep. 30, 1988 [JP] Japan ............................ 63-247038

[51] Int. Cl.[5] ...................... G03G 5/06; C07C 211/00

[52] U.S. Cl. ...................................... 430/74; 430/72; 430/73; 430/59; 564/309

[58] Field of Search ...................... 430/59, 72, 73, 74; 564/309

[56] References Cited

U.S. PATENT DOCUMENTS

| | | | |
|---|---|---|---|
| 3,959,364 | 5/1976 | Armitage et al. | 544/59 X |
| 4,833,054 | 5/1989 | Akasaki et al. | 430/59 |
| 4,869,988 | 9/1989 | Ong et al. | 430/59 |
| 4,898,800 | 2/1990 | Shimada et al. | 430/59 |

FOREIGN PATENT DOCUMENTS

| | | | |
|---|---|---|---|
| 62-267749 | 11/1987 | Japan | 430/73 |
| 63-40164 | 2/1988 | Japan | 430/59 |

*Primary Examiner*—Roland Martin
*Attorney, Agent, or Firm*—Oblon, Spivak, McClelland, Maier & Neustadt

[57] ABSTRACT

An electrophotographic photoconductor is disclosed, which comprises an electroconductive support and a photoconductive layer formed thereon comprising as an effective component at least one biphenyl compound represented by the following formula (I):

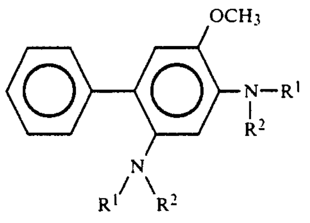

(I)

wherein $R^1$ and $R^2$ each represent an alkyl group which may have a substituent, an alkoxyl group which may have a substituent, or an aryl group which may have a substituent, provided that at least one of $R^1$ and $R^2$ represents an unsubstituted or substituted aryl group. Furthermore, charge transporting materials comprising the above biphenyl compound and novel biphenyl compounds having formula (II) for use in the electrophotographic photoconductor are disclosed.

14 Claims, 3 Drawing Sheets

BIPHENYL COMPOUNDS AND ELECTROPHOTOGRAPHIC PHOTOCONDUCTOR COMPRISING THE SAME

BACKGROUND OF THE INVENTION

1. Field of the Invention

The present invention relates to biphenyl compounds and an electrophotographic photoconductor, in particular, to an electrophotographic photoconductor comprising an electroconductive support and a photoconductive layer comprising any of the biphenyl compounds.

2. Discussion of Background

Conventionally, inorganic materials such as selenium, cadmium sulfide and zinc oxide are used as a photoconductive material of an electrophotographic photoconductor in the electrophotographic process. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electrical charge of the exposed areas, so that a latent electrostatic image is formed on the photoconductor. The thus formed latent electrostatic image is developed by a developer comprising a coloring agent such as a dye and a pigment, and a binder agent such as a polymeric material, to a visible image.

Fundamental characteristics required for the photoconductor in such an electrophotographic process are: (1) chargeability to an appropriate potential in the dark, (2) minimum dissipation of electrical charge in the dark, and (3) rapid dissipation of electrical charge when exposed to light.

However, while the above-mentioned inorganic materials have many advantages, they have several shortcomings from the viewpoint of practical use.

For instance, a selenium photoconductor, which is widely used at present, satisfies the above-mentioned requirements (1) to (3) completely, but it has the shortcomings that its manufacturing conditions are difficult and, accordingly, its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be easily obtained by coating a dispersion of cadmium sulfide particles and zinc oxide particles in a binder resin on a support. However, they are poor in mechanical properties, such as surface smoothness, hardness, tensile strength and wear resistance. Therefore, they cannot be used in the repeated operation, as they are.

To solve the problems of the inorganic materials, various electrophotographic photoconductors employing organic materials are proposed recently and some are still put to practical use. For example, there are known a photoconductor comprising poly-N-vinylcarbazole and 2,4,7-trinitrofluorene-9-on, as disclosed in U.S. Pat. No. 3,484,237; a photoconductor prepared by sensitizing poly-N-vinylcarbazole with a pigment of pyrylium salt, as described in Japanese Patent Publication 48-25658; a photoconductor comprising as the main component an organic pigment, as described in Japanese Laid-Open patent application 47-37543; a photoconductor comprising as the main component an eutectic crystal complex of a dye and a resin, as described in Japanese Laid-Open patent application 47-10735; a photoconductor prepared by sensitizing a triphenylamine compound with a sensitizer pigment, as described in U.S. Pat. No. 3,180,730; and a photoconductor comprising poly-N-vinylcarbazole and an amine derivative as a charge transporting material, as described in Japanese Laid-Open patent application 58-1155.

These electrophotographic photoconductors have their own excellent characteristics and considered to be valuable for practical use. With various requirements of the electrophotographic photoconductor in electrophotography taken into consideration, however, the above-mentioned conventional electrophotographic photoconductors cannot meet all the requirements for use in electrophotography.

SUMMARY OF THE INVENTION

It is therefore a first object of the present invention to privide an electrophotographic photoconductor free from the conventional shortcomings, which can completely satisfy all the requirements in the electrophotographic process.

A second object of the present invention is to provide an electrophotographic photoconductor having good durability, which can be easily manufactured at relatively low cost.

A third object of the present invention is to provide a charage transporting material for use in the above-mentioned electrophotographic photoconductor.

A fourth object of the present invention is to provide novel biphenyl compounds employed as a photoconductive material in the electrophotographic photoconductor.

The first and second objects of the present invention can be achieved by an electrophotographic photoconductor comprising an electroconductive support and a photoconductive layer formed thereon comprising as an effective component at least one biphenyl compound represented by the following formula (I):

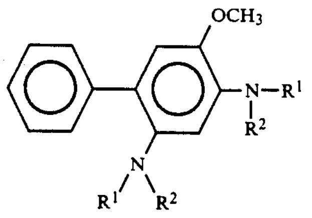

(I)

wherein $R^1$ and $R^2$ each represent an alkyl group which may have a substituent, an alkoxyl group which may have a substituent, or an aryl group which may have a substituent, provided that at least one of $R^1$ and $R^2$ represents an unsubstituted or substituted aryl group.

The third object of the present invention can be attained by a material comprising a biphenyl compound represented by the following formula (I):

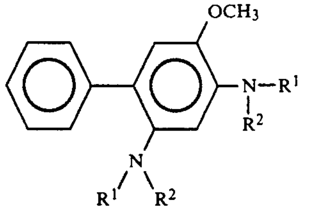

(I)

wherein $R^1$ and $R^2$ each represent an alkyl group which may have a substituent, an alkoxyl group which may have a substituent, or an aryl group which may have a substituent, provided that at least one of $R^1$ and $R^2$ represents an unsubstituted or substituted aryl group.

The fourth object of the present invention can be attained by biphenyl compounds having the formula (II):

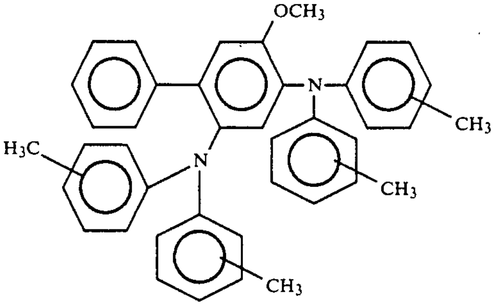

(II)

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
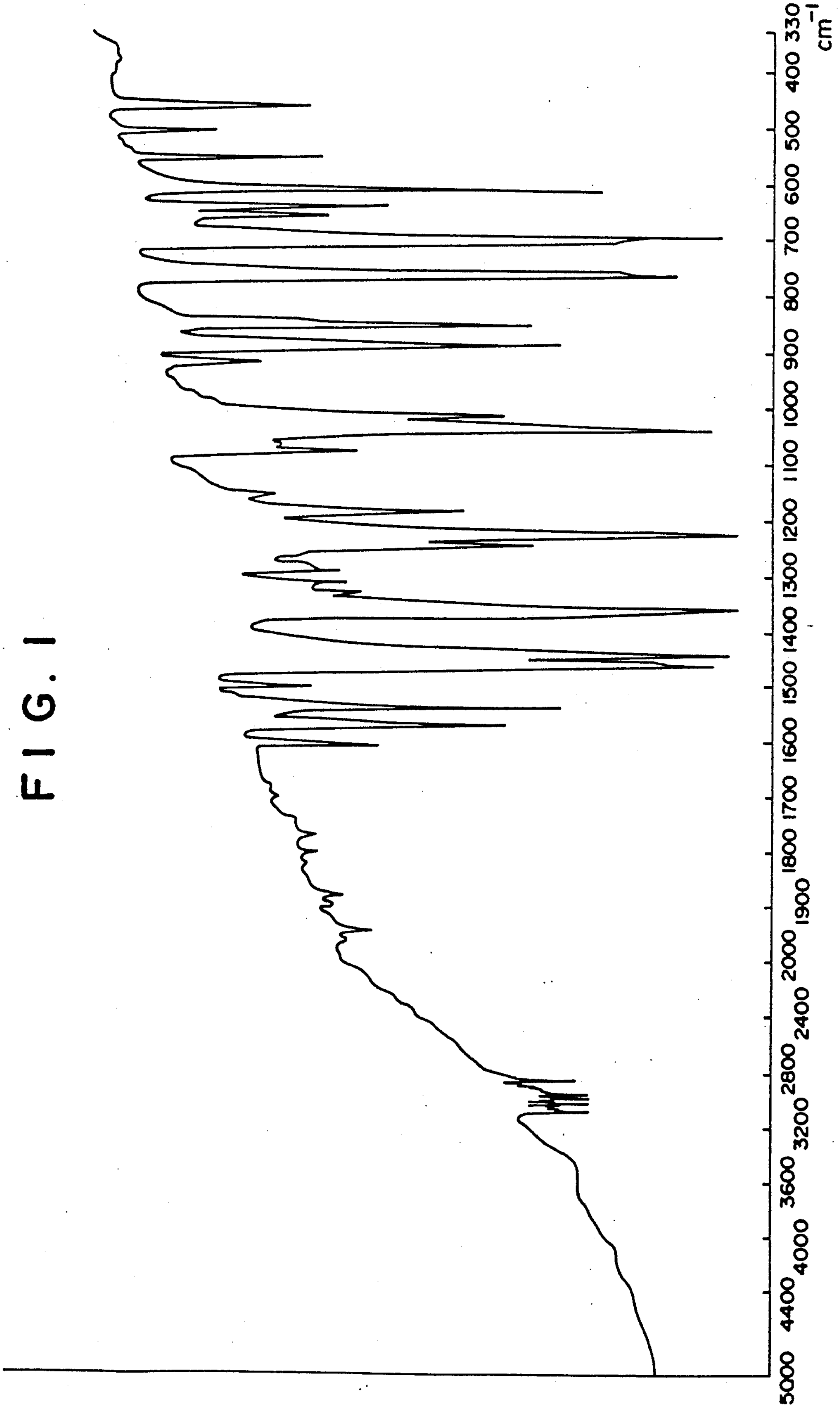
FIG. 1 is an IR spectrum of an iodine compound for use in the present invention.

An electrophotographic photoconductor according to the present invention comprises an electroconductive support and a photoconductive layer formed thereon, comprising at least one of biphenyl compounds having formula (I):

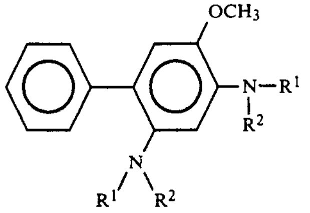

(I)

wherein $R^1$ and $R^2$ each represent an alkyl group, preferably an alkyl group having 1 to 4 carbon atoms, which may have a substituent, an alkoxyl group, preferably an alkoxyl group having 1 to 4 carbon atoms, which may have a substituent, or an aryl group which may have a substituent, provided that at least one of $R^1$ and $R^2$ represents an unsubstituted or substituted aryl group.

Examples of the aryl group in the formula (I) are as follows:

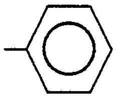, 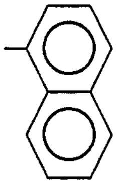, 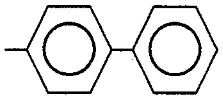, and

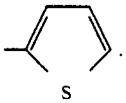.

An example of the substituent of the alkyl group or alkoxy group in the formula (I) is a phenyl group.

Examples of the substituent of the aryl group in the formula (I) are an alkyl group having 1 to 4 carbon atoms and an alkoxy group having 1 to 4 carbon atoms.

Specific examples of the biphenyl compounds for use in the present invention are shown in the following Table 1.

TABLE 1

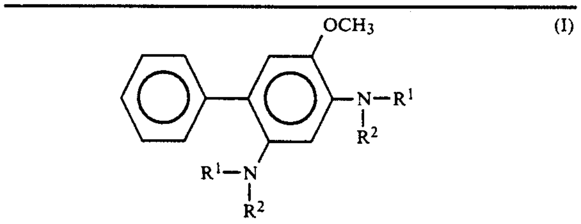

(I)

| Compound No. | $R^1$ | $R^2$ |
|---|---|---|
| 1 | 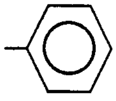 | $-CH_3$ |
| 2 | 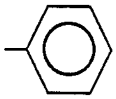 | 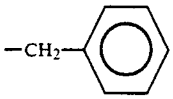 |

TABLE 1-continued

| Compound No. | $R^1$ | $R^2$ |
| --- | --- | --- |
| 3 | 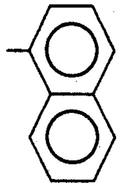 | 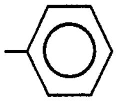 |
| 4 | 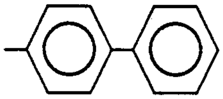 | 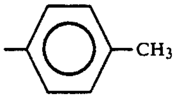 |
| 5 | 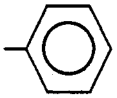 | 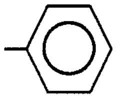 |
| 6 | 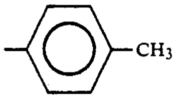 | 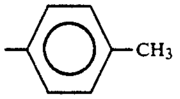 |
| 7 | 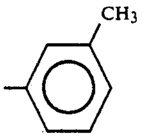 | 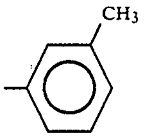 |
| | 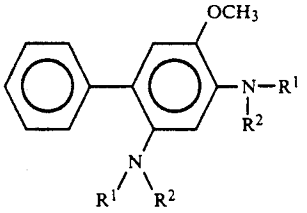 | (I) |
| 8 | 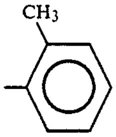 | 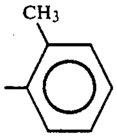 |
| 9 | 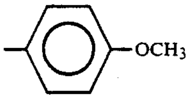 | 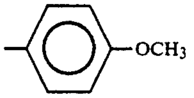 |
| 10 | 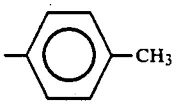 | 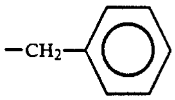 |
| 11 | 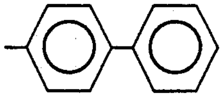 | 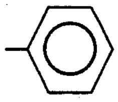 |
| 12 | 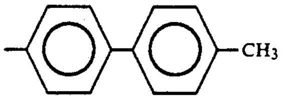 | 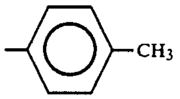 |

TABLE 1-continued

| Compound No. | $R^1$ | $R^2$ |
| --- | --- | --- |
| 13 | 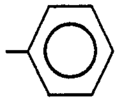 | 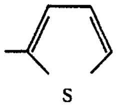 |
| 14 | 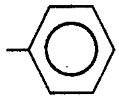 | 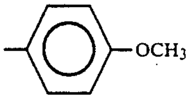 |

The biphenyl compounds of formula (I) for use in the present invention can be obtained by allowing 2,4-diiode-5-methoxybiphenyl having formula (III) to react with an amine compound having the formula (IV) in accordance with the following reaction scheme:

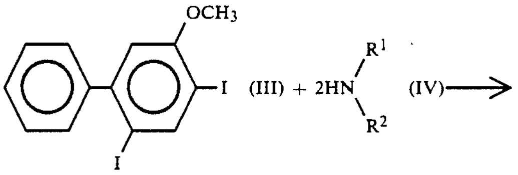

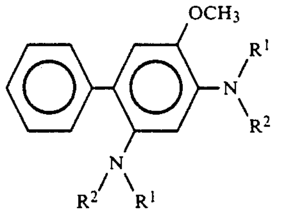
(I)

wherein $R^1$ and $R^2$ are the same as previously defined.

Alternatively, the biphenyl compounds of formula (I) can be also obtained as follows: 2,4-diode-5-methoxybiphenyl having formula (III) is reacted with an acetylamine compound having formula (V) to produce a diacetyl compound having formula (VI). The diacetyl compound is hydrolyzed and is then allowed to react with a halogen compound having formula (VIII):

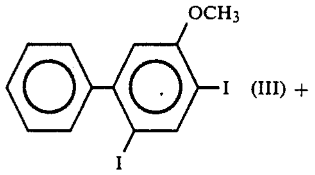
(III) +

$2R'-NHCOCH_3$ (V)

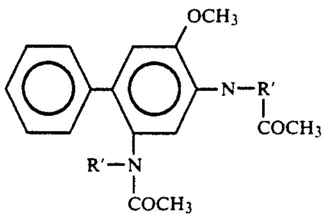
(VI)

Hydrolyzed diacetyl compound + $2R^2-X$ (VII)

-continued

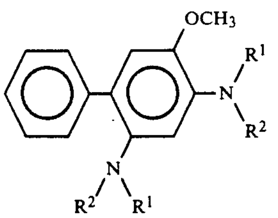

(I)

In the above, $R^1$ and $R^2$ are the same as previously defined; and X represents a halogen.

More specifically, biphenyl compound No. 6 in Table 1 can be obtained as follows: 2,4-diiode-5-methoxybiphenyl is allowed to react with N,N-ditolylamine in a solvent in a stream of nitrogen at 150° to 250° C. in the presence of copper particles, copper oxide or copper halogenide, with an alkaline salt or an alkaline material added thereto in a sufficient amount for being capable of neutralizing hydrogen halogenide generated in the course of the reaction. In this case, the solvent may not be used in the reaction.

Examples of the above-mentioned alkaline salt used in the reaction are sodium carbonate and potassium carbonate; and examples of the alkaline material are sodium hydroxide and other caustic alkaline materials. Examples of the solvent used in the reaction are nitrobenzene, dichlorobenzene, quinoline, N,N-dimethylformamide, dimethyl sulfoxide, N-methylpyrrolidone and 1,3-dimethyl-2-imidazolidinone.

The biphenyl compounds for use in the present invention, which are remarkably effective as photoconductive materials in the electrophotographic photoconductor, are optically or chemically sensitized with a sensitizer such as a dye or Lewis acid. In addition, the biphenyl compounds effectively function as a charge transporting material in a function-separating type electrophotographic photoconductor where an organic or inorganic pigment serves as a charge generating material.

In the photoconductors according to the present invention, at least one biphenyl compound of the formula (I) is contained in the photoconductive layers 2, 2*a*, 2*b*, 2*c*, 2*d* and 2*e*. The biphenyl compounds can be employed in different ways, for example, as shown in FIGS. 3 through 8.

Figure 3:
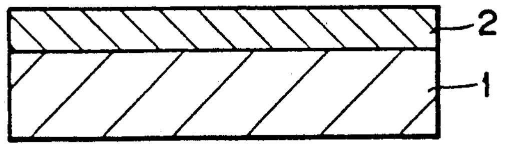
FIG. 3 is a schematic cross-sectional view of the first example of an electrophotographic photoconductor according to the present invention.

In the photoconductor as shown in FIG. 3, a photoconductive layer 2 is formed on an electroconductive support 1, which photoconductive layer 2 comprises a biphenyl compound, a sensitizing dye and a binder agent (binder resin). In this photoconductor, the biphenyl compound works as a photoconductive material, through which charge carriers which are necessary for the light decay of the photoconductor are generated and transported. However, the biphenyl compound itself scarcely absorbs light in the visible light range and, therefore, it is necessary to add a sensitizing dye which absorbs light in the visible light range in order to form latent electrostatic images by use of visible light.

Figure 4:
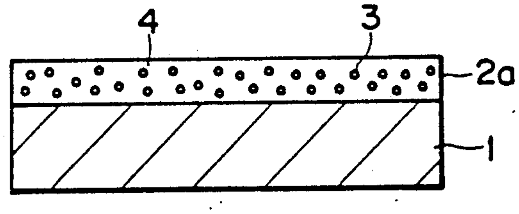
FIG. 4 is a schematic cross-sectional view of the second example of an electrophotographic photoconductor according to the present invention.

Referring to FIG. 4, there is shown an enlarged cross-sectional view of another embodiment of an electrophotographic photoconductor according to the present invention. In the figure, reference numeral 1 indicates an electroconductive support. On the electroconductive support 1, there is formed a photoconductive layer 2*a* comprising a charge generating material 3 dispersed in a charge transporting medium 4 comprising a biphenyl compound and a binder agent. In this embodiment, the biphenyl compound and the binder agent (or a mixture of the binder agent and a plasticizer) in combination constitute the charge transporting medium 4. The charge generating material 3, which is, for example, an inorganic or organic pigment, generates charge carriers. The charge transporting medium 4 accepts the charge carriers generated by the charge generating material 3 and transports those charge carriers In this electrophotographic photoconductor, it is basically necessary that the light-absorption wavelength regions of the charge generating material 3 and the biphenyl compound not overlap in the visible light range. This is because, in order that the charge generating material 3 produce charge carriers efficiently, it is necessary that light pass through the charge transporting medium 4 and reach the surface of the charge generating material 3. Since the biphenyl compounds of the previously described general formula (I) do not substantially absorb light in the visible range, they can work effectively as charge transporting materials in combination with the charge generating material 3 which absorbs the light in the visible region and generates charge carriers.

Figure 5:
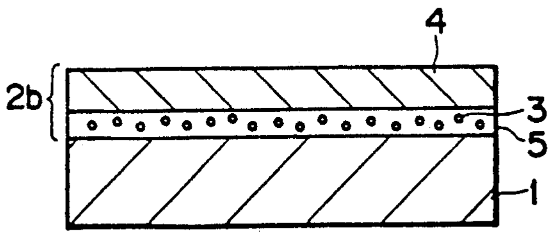
FIG. 5 is a schematic cross-sectional view of the third example of an electrophotographic photoconductor according to the present invention.

Referring to FIG. 5, there is shown an enlarged cross-sectional view of a further embodiment of an electrophotographic photoconductor according to the present invention. In the figure, there is formed on the electroconductive support 1 a two-layered photoconductive layer 2*b* comprising a charge generation layer 5 containing the charge generating material 3, and a charge transport layer 4 containing a biphenyl compound of the previously described formula (I).

In this photoconductor, light which has passed through the charge transport layer 4 reaches the charge generation layer 5, and charge carriers are generated within the charge generation layer 5. The charge carriers which are necessary for the light decay for latent electrostatic image formation are generated by the charge generating material 3, accepted and transported by the charge transport layer 4. In the charge transport layer 4, the biphenyl compound mainly works for transporting charge carriers. The generation and transportation of the charge carriers are performed by the same mechanism as that in the photoconductor shown in FIG. 4.

Figure 6:
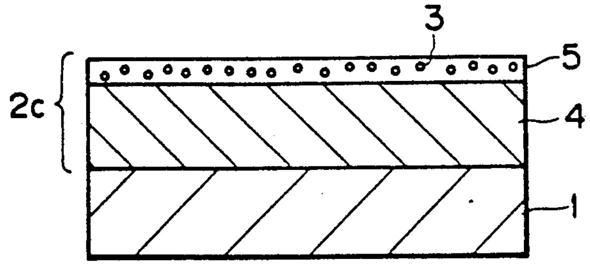
FIG. 6 is a schematic cross-sectional view of the fourth example of an electrophotographic photoconductor according to the present invention.

Referring to FIG. 6, there is shown still another embodiment of an electrophotographic photoconductor according to the present invention. In the figure, the overlaying order of the charge generation layer 5 and the charge transport layer 4 is reversed in view of the electrophotographic photoconductor as shown in FIG. 5. The mechanism of the generation and transportation of charge carriers is substantially the same as that of the photoconductor shown in FIG. 5.

Figure 7:
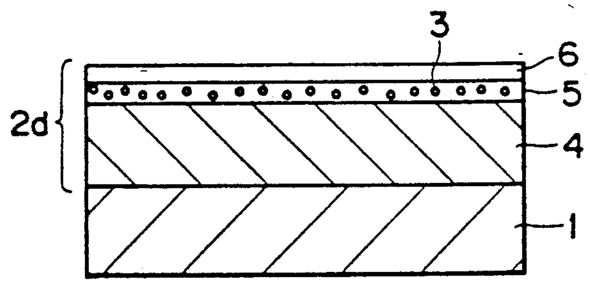
FIG. 7 is a schematic cross-sectional view of the fifth example of an electrophotographic photoconductor according to the present invention.

In the above photoconductor, a protective layer 6 may be formed on the charge generation layer 5 as shown in FIG. 7 for protecting the charge generation layer 5.

Figure 8:
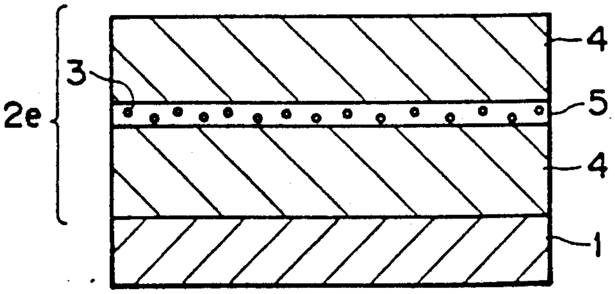
FIG. 8 is a schematic cross-sectional view of the sixth example of an electrophotographic photoconductor according to the present invention.

Referring to FIG. 8, there is shown a still further embodiment of an electrophotographic photoconductor according to the present invention. In the figure, a photoconductive layer 2*e* comprises a pair of charge transport layers 4 and 4' and a charge generation layer 5 which is interposed between the charge transport layers 4 and 4'.

When the electrophotographic photoconductor according to the present invention as shown in FIG. 3 is prepared, at least one biphenyl compound of the previously described formula (I) is dispersed in a binder resin solution, and a sensitizing dye is then added to the mixture, so that a photoconductive layer coating liquid is prepared. The thus prepared photoconductive layer coating liquid is coated on an electroconductive support 1 and dried, so that a photoconductive layer 2 is formed on the electroconductive support 1.

It is preferable that the thickness of the photoconductive layer 2 be in the range of 3 to 50 μm, more preferably in the range of 5 to 20 μm. It is preferable that the amount of the biphenyl compound contained in the photoconductive layer 2 be in the range or 30 to 70 wt. %, more preferably about 50 wt. %.

It is preferable that the amount of the sensitizing dye contained in the photoconductive layer 2 be in the range of 0.1 to 5 wt. %, more preferably in the range of 0.5 to 3 wt. %.

Specific examples of the sensitizing dye for use in the present invention are: triarylmethane dyes such as Briliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; pyrylium dyes such as 2,6-diphenyl-4-(N,N-dimethylaminophenyl)thiapyrylium perchlorate and benzopyrylium salts (Japanese Patent Publication 48-25658); and 2,4,7-trinitro-9-fluorenone and 2,4-dinitro-9-fluorenone.

The electrophotographic photoconductor shown in FIG. 4 can be obtained by dispersing finely-divided particles of the charge generating material 3 in the solution in which at least one biphenyl compound for use in the present invention and the binder agent are dissolved, coating the above-prepared dispersion on the electroconductive support 1 and then drying the same to form the photoconductive layer 2*a*.

It is preferable that the thickness of the photoconductive layer 2*a* be in the range of 3 to 50 μm, more preferably in the range of 5 to 20 μm. It is preferable that the amount of the biphenyl compound contained in the photoconductive layer 2*a* be in the range or 10 to 95 wt. %, more preferably in the range of 30 to 90 wt. %.

It is preferable that the amount of the charge generating material 3 contained in the photoconductive layer 2*a* be in the range of 0.1 to 50 wt. %, more preferably in the range of 1 to 20 wt. %.

Specific examples of the charge generating material 3 for use in the present invention are as follows: inorganic pigments such as selenium, selenium - tellurium, cadmium sulfide, cadmium sulfide - selenium and α-silicone; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open patent application 53-95033), an azo pigment having a distyryl benzene skeleton (Japanese Laid-Open patent application 53-133445), an azo pigment having a triphenylamine skeleton (Japanese Laid-Open patent application 53-132347), an azo pigment having a dibenzothiophene skeleton (Japanese Laid-Open patent application 54-21728), an azo pigment having an oxadiazole skeleton (Japanese Laid-Open patent application 54-12742), an azo pigment having a fluorenone skeleton (Japanese Laid-Open patent application 54-22834), an azo pigment having a bisstilbene skeleton (Japanese Laid-Open patent application 54-17733), an azo pigment having a distyryl oxadiazole skeleton (Japanese Laid-Open patent application 54-2129), and an azo pigment having a distyryl carbazole skeleton (Japanese Laid-Open patent application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B and Indanthrene Scarlet R (made by Bayer Co., Ltd.). These charge generating materials may be used alone or in combination.

The electrophotographic photoconductor shown in FIG. 5 can be obtained as follows:

The charge generating material is vacuum-deposited on the electroconductive support 1, or the dispersion in which finely-divided particles of the charge generating material 3 is dispersed in an appropriate solvent, together with the binder agent when necessary, is coated on the electroconductive support 1 and dried, so that the charge generation layer 5 is formed. When necessary, the charge generation layer 5 is subjected to surface treatment by buffing and adjustment of the thickness thereof. On the thus formed charge generation layer 5, a coating solution in which at least one biphenyl compound and the binder agent are dissolved is coated and dried, so that the charge transport layer 4 is formed. In the charge generation layer 5, the same charge generating material as employed in the above-mentioned photoconductive layer 2*a* can be used.

The thickness of the charge generation layer 5 is 5 μm or less, more preferably 2 μm or less. It is preferable that the thickness of the charge transport layer 4 be in the range of 3 to 50 μm, more preferably in the range of 5 to 20 μm. When the charge generation layer 5 is obtained by coating the dispersion in which finely-divided particles of the charge generating material 3 is dispersed in an appropriate solvent together with the binder agent, it is preferable that the amount of finely-divided particles of the charge generating material 3 contained in the charge generation layer 5 be in the range of 10 to 95 wt. %, more preferably in the range of about 50 to 90 wt. %. It is preferable that the amount of the biphenyl compound contained in the charge transport layer 4 be in the range of 10 to 95 wt. %, more preferably in the range of 30 to 90 wt. %.

The electrophotographic photoconductor shown in FIG. 6 can be obtained as follows:

A coating solution in which the biphenyl compound and the binder agent are dissolved is coated on the electroconductive support 1 and dried to form the charge transport layer 4. On the thus formed charge transport layer 4, a dispersion prepared by dispersing finely-divided particles of the charge generation material 3 in the solvent, in which the binder agent is dissolved when necessary, is coated by spray coating and dried to form the charge generation layer 5 on the charge transport layer 4. The amount ratio of components contained in the charge generation layer and charge transport layer is the same as previously described in FIG. 5.

The electrophotographic photoconductor shown in FIG. 7 can be obtained by forming a protective layer 6 on the charge generation layer 5 as obtained in FIG. 6 by spray-coating of an appropriate resin solution. As a resin employed in the protective layer 6, any of binder agents to be described later can be used.

The electrophotographic photoconductor according to the present invention as shown in FIG. 8 can be obtained by forming on an electroconductive support 1 a charge transport layer 4, a charge generation layer 5, and a charge transport layer 4' successively in that order.

Specific examples of the electroconductive support 1 for the electrophotographic photoconductor according to the present invention include a metallic plate or foil made of aluminum, a plastic film on which a metal such as aluminum is deposited, and a sheet of paper which has been treated so as to be electroconductive.

Specific examples of the binder agent for use in the present invention are condensation resins such as polyamide, polyurethane, polyester, epoxy resin, polyketone and polycarbonate; and vinyl copolymers such as polyvinylketone, polystyrene, poly-N-vinylcarbazole and polyacrylamide. All the resins having insulating properties and adhesive force can be employed. Some plasticizers may be added to the above-mentioned binder agent, when necessary. Examples of the plasticizer for use in the present invention are halogenated paraffin, polybiphenyl chloride, dimethylnaphthalene and dibutyl phthalate.

Furthermore, in the electrophotographic photoconductors according to the present invention, an adhesive layer or barrier layer may be interposed between the electroconductive support and the photoconductive layer when necessary. Examples of the material for use in the adhesive layer or barrier layer are polyamide, nitrocellulose and aluminum oxide. It is preferable that the thickness of the adhesive layer or barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and when necessary, the developed image can be transferred to a sheet of paper. The electrophotographic photoconductors according to the present invention have the advantages in that the photosensitivity is high and the flexibility is improved.

Other features of this invention will become apparent in the course of the following description of exemplary embodiments, which are given for illustration of the invention and are not intended to be limiting thereof.

EXAMPLE

Synthesis Example 1

[Preparation of 2,4-diiode-5-methoxybiphenyl]

25.3 g of m-phenylanisole, 5.47 g of periodic acid and 14.1 g of iodine were added to 150 ml of an aqueous solution of 80 vol % acetic acid. This mixture was stirred at 65° C. for 9 hours. After cooled to room temperature, the mixture was poured into iced water and extracted with toluene. The organic layer of the thus extracted mixture was washed with water and dried. After drying, the solvent was removed, whereby an orange oil-like product was obtained.

The thus obtained product was subjected to column chromatography using silica gel as a carrier and toluene as an eluting solution and recrystallized from a mixed solvent of ethanol and cyclohexane, so that 7.23 g of 2,4-diiode-5-methoxybiphenyl precipitated as colorless crystals in the form of prisms. The melting point of the product was 122.5 to 123.5° C.

The results of the elemental analysis of the thus obtained product were as follows:

| | % C | % H |
|---|---|---|
| Calculated | 35.81 | 2.32 |
| Found | 35.76 | 2.21 |

The above calculation was based on the formula for 2,4-diiode-5-methoxybiphenyl of $C_{13}H_{10}I_2O$.

FIG. 1 shows an infrared spectrum of 2,4-diiode-5-methoxybiphenyl, taken by use of a KBr tablet.

| | |
|---|---|
| Absorptions characteristic of COC stretching vibration | 1225 $cm^{-1}$ and 1040 $cm^{-1}$ |
| Absorptions characteristic of benzene ring (CH) out-of-plane deformation vibration | 890 $cm^{-1}$, 850 $cm^{-1}$, 765 $cm^{-1}$ and 700 $cm^{-1}$ |

The nuclear magnetic resonance (NMR) of the product was as follows:

NMR in $CDCl_3$;
δ3.8 (s, 3H, $OCH_3$)
δ6.7 (s, 1H, benzene ring)
δ7.3 (m, 5H, benzene ring)
δ8.2 (s, 1H, benzene ring)

[Synthesis of 2,4-bis(N,N-di-p-tolylamino-5-methoxybiphenyl]

4.36 g (0.010 mol) of 2,4-diiode-5-methoxybiphenyl, 4.34 g (0.022 mol) of p-ditolylamine, 3.65 g (0.026 mol) of potassium carbonate and 0.10 g of copper particles were added to 50 ml of nitrobenzene. This mixture was refluxed in a stream of nitrogen for 9 hours. After the mixture was cooled to room temperature, the resulting insoluble material of the mixture was removed by filtration together with Celite and nitrobenzene was removed therefrom under reduced pressure, whereby a brown, oil-like product was obtained. The thus obtained product was subjected to column chromatography twice. First, silica gel and toluene were used as a carrier and an eluting solution, respectively, and the second, silica gel and a mixture of toluene and n-hexane with a mixing ratio of 1:1 were used as the carrier and eluting solution, respectively. The product was recrystallized from a mixed solvent of toluene and n-hexane, so that 1.44 g of 2,4-bis(N,N-di-p-tolylamino)-5-methoxybiphenyl was obtained in the form of colorless plates. The melting point of the product was 189.5° to 190.5° C.

The results of the elemental analysis of the thus obtained product were as follows:

| | % C | % H | % N |
|---|---|---|---|
| Calculated | 85.66 | 6.68 | 4.87 |
| Found | 85.72 | 6.54 | 4.68 |

The above calculation was based on the formula for 2,4-bis(N,N-di-p-tolylamino)-5-methoxybiphenyl of $C_{41}H_{38}N_2O$.

Figure 2:
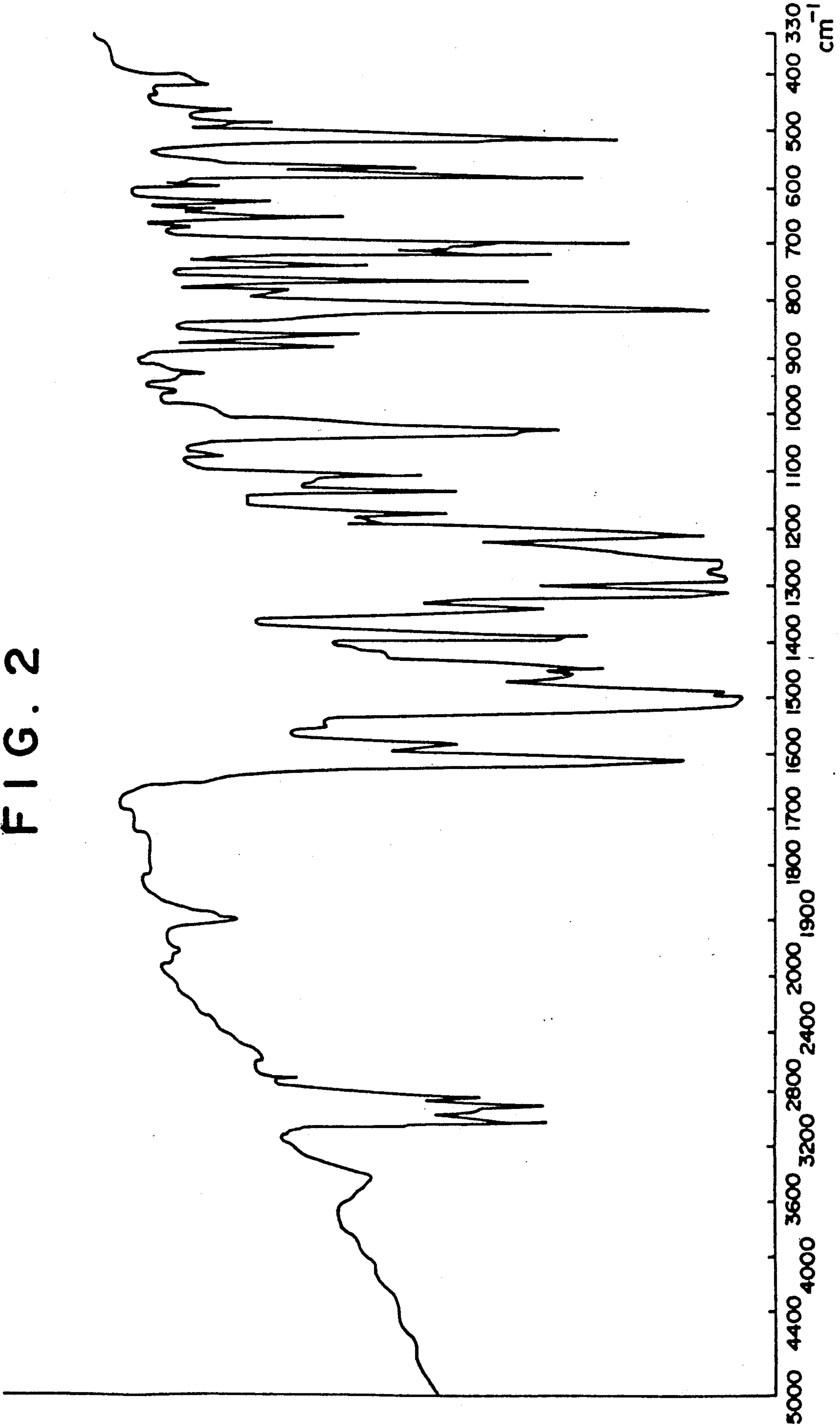
FIG. 2 is an IR spectrum of a biphenyl compound according to the present invention.

FIG. 2 shows an infrared spectrum of 2,4-bis(N,N-diptolylamino)-5-methoxybiphenyl, taken by use of a KBr tablet.

Example 1

7.5 parts by weight of a bisazo compound having the following formula and 500 parts by weight of a 0.5% tetrahydrofuran solution of a polyester resin (Trademark "Vylon 200" made by Toyobo Company, Ltd.) were dispersed and ground in a ball mill. The thus prepared dispersion was coated on an aluminum surface of an aluminum-deposited polyester film by a doctor blade, and dried at room temperature, so that a charge generation layer having a thickness of about 1 μm was formed on the aluminum-deposited polyester film.

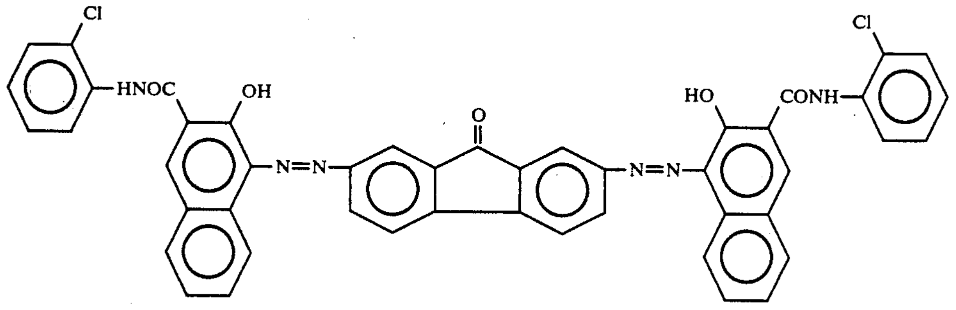

1 part by weight of 2,4-bis(N,N-di-p-tolylamino)-5-methoxybiphenyl (biphenyl compound No. 6 in Table 1) prepared in the above-mentioned Synthesis Example 1 was dissolved in a resin solution consisting of 1 part by weight of polycarbonate resin (Trademark "Panlite K-1300" made by Teijin Limited.) and 8 parts by weight of tetrahydrofuran. This solution was coated on the above formed charge generation layer by a doctor blade and then dried at 80° C. for 2 minutes and then at 120° C. for 5 minutes, so that a charge transport layer having a thickness of about 20 μm was formed on the charge generation layer. Thus a two-layered type electrophotographic photoconductor No. 1 according to the present invention was prepared.

Example 2

76 by weight of Diane Blue (C.I. Pigment Blue 25, CI21180) serving as a charge generating material, 1260 parts by weight of a 2% tetrahydrofuran solution of a polyester resin (Trademark "Vylon 200" made by Toyobo Company, Ltd.) and 3700 parts by weight of tetrahydrofuran were dispersed and ground in a ball mill. The thus prepared dispersion was coated on an aluminum surface of an aluminum-deposited polyester film by a doctor blade, and dried at room temperature, so that a charge generation layer having a thickness of about 1 μm was formed on the aluminum-deposited polyester film.

2 parts by weight of 2,4-bis(N,N-di-p-tolylamino)-5-methoxybiphenyl (biphenyl compound No. 6 in Table 1) prepared in the above-mentioned Synthesis Example 1, 2 parts by weight of polycarbonate resin (Trademark "Panlite K-1300" made by Teijin Limited.) and 16 parts by weight of tetrahydrofuran were mixed to form a solution. This solution was coated on the above formed charge generation layer by a doctor blade and then dried at 80° C. for 2 minutes and then at 120° C. for 5 minutes, so that a charge transport layer having a thickness of about 20 μm was formed on the charge generation layer. Thus a two-layered type electrophotographic photoconductor No. 2 according to the present invention was prepared.

Examples 3 to 16

Example 2 was repeated except that Diane Blue serving as a charge generating material and the biphenyl compound No. 6 serving as a charge transporting material employed in Example 2 were replaced by the respective charge generating materials and charge transporting materials listed in the following Table 2, whereby electrophotographic photoconductors No. 3 to No. 16 according to the present invention were prepared.

TABLE 2
| Photoconductor No. | Charge Generating Material | Charge Transporting Material (Biphenyl Compound No.) |
|---|---|---|
| 2 | 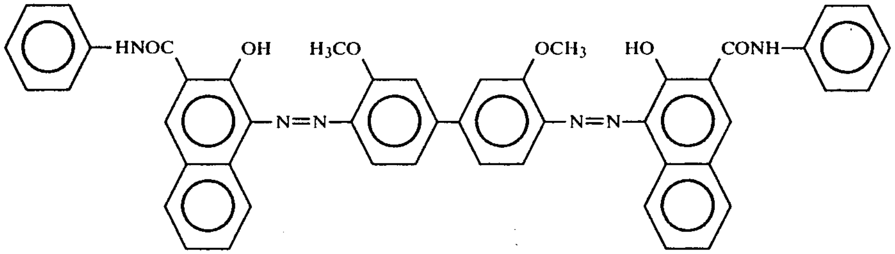 | 6 |
| 3 | 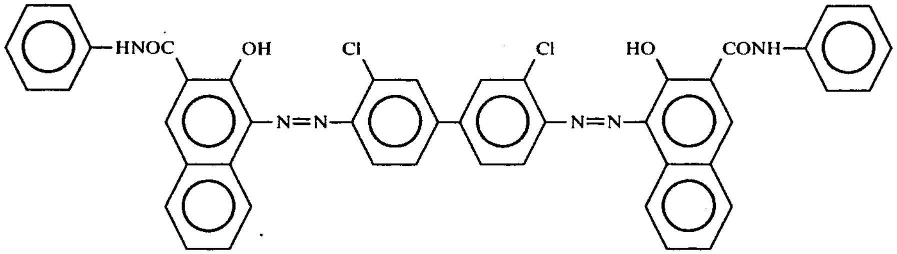 | 6 |
| 4 | 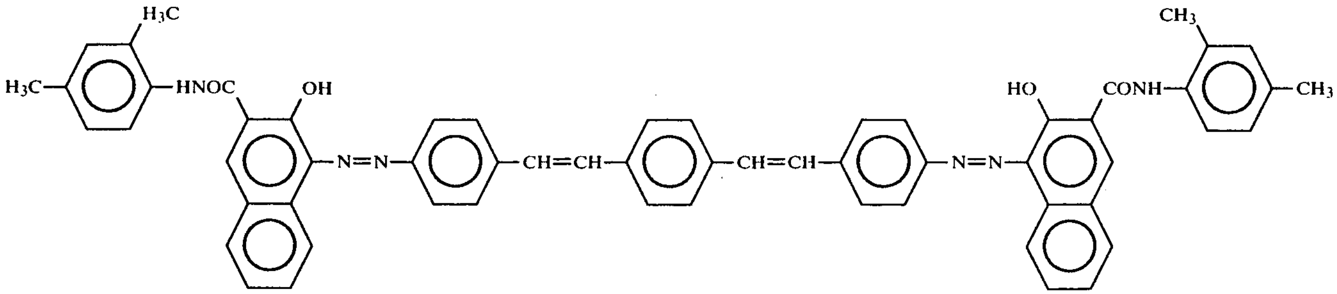 (hereinafter referred to as P-1) | 6 |

TABLE 2-continued
| Photoconductor No. | Charge Generating Material | Charge Transporting Material (Biphenyl Compound No.) |
|---|---|---|
| 5 | 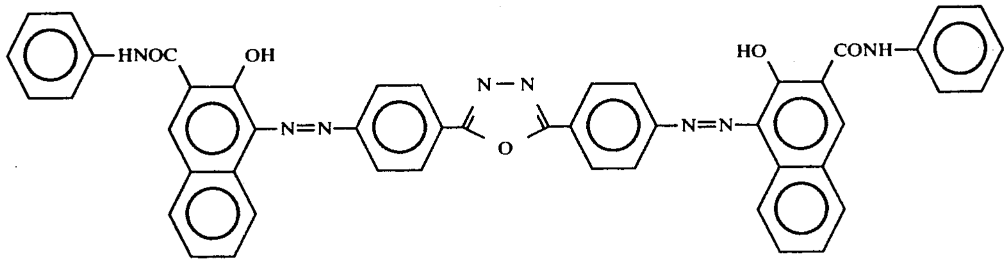 | 6 |
| 6 | 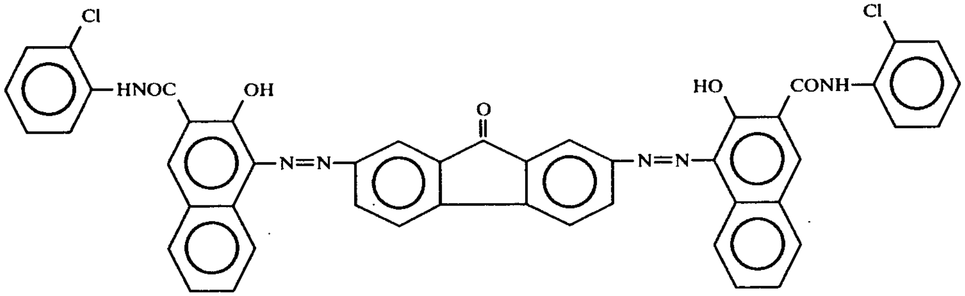 (hereinafter referred to as P-2) | 6 |

TABLE 2-continued
| Photoconductor No. | Charge Generating Material | Charge Transporting Material (Biphenyl Compound No.) |
| --- | --- | --- |
| 7 | 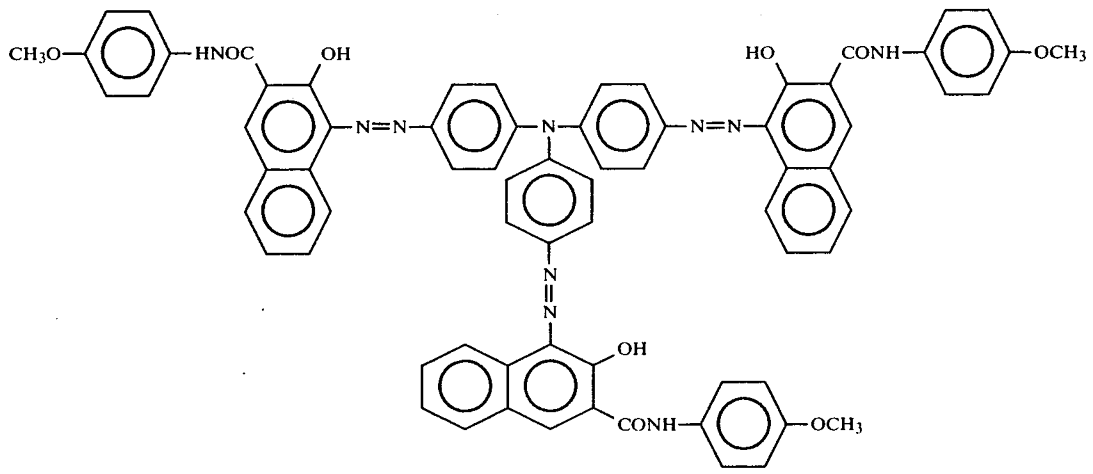 | 6 |
| 8 | β-type Copper Phthalocyanine | 6 |
| 9 | 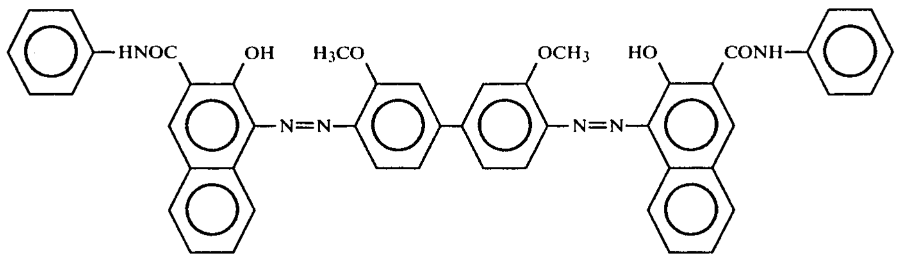 | 5 |

TABLE 2-continued
| Photoconductor No. | Charge Generating Material | Charge Transporting Material (Biphenyl Compound No.) |
|---|---|---|
| 10 | 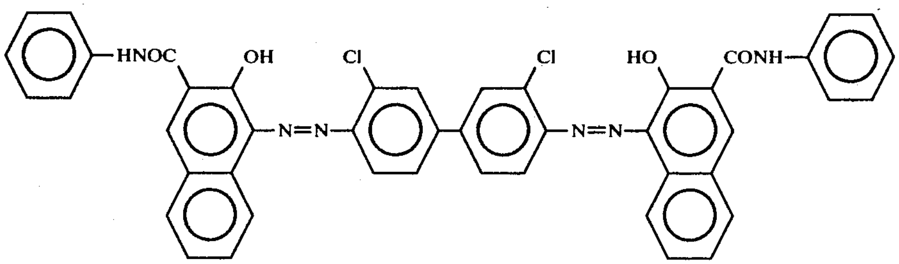 | 5 |
| 11 | P-1 | 5 |
| 12 | P-2 | 5 |
| 13 | P-1 | 14 |
| 14 | P-2 | 14 |
| 15 | P-1 | 7 |
| 16 | P-2 | 7 |

Example 17

The following perylene pigment was vacuum-deposited on an aluminum plate having a thickness of 300 μm, so that a charge generation layer having a thickness of about 1 μm was formed on the aluminum plate.

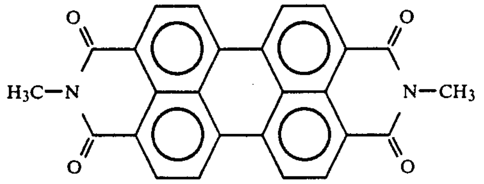

2 parts by weight of 2,4-bis(N,N-di-p-tolylamino)-5-methoxybiphenyl (biphenyl compound No. 6) prepared in the above-mentioned Synthesis Example 1, 3 parts by weight of polyester resin (Trademark "Polyester Adhesive 49000" made by Du Pont de Nemours, E.I. & Co.) and 45 parts by weight of tetrahydrofuran were mixed to form a solution. This solution was coated on the above formed charge generation layer by a doctor blade, dried at room temperature, and then dried under reduced pressure, so that a charge transport layer having a thickness of about 10 μm was formed on the charge generation layer. Thus an electrophotographic photoconductor No. 17 according to the present invention was prepared.

Example 18

A mixture of 1 part by weight of the same Diane Blue as employed in Example 2 and 158 parts by weight of tetrahydrofuran was dispersed and ground in a ball mill to form a dispersion. To the thus formed dispersion, 12 parts by weight of biphenyl compound No. 5 in Table 1 and 18 parts by weight of polyester resin (Trademark "Polyester Adhesive 49000" made by Du Pont de Nemours, E.I. & Co.) were added to form a solution. This solution was coated on an aluminum-deposited polyester film by a doctor blade, and dried at 100° C. for 30 minutes, so that a photoconductive layer having a thickness of about 16 μm was formed on the electroconductive support. Thus, an electrophotographic photoconductor No. 18 according to the present invention was prepared.

Example 19

2 parts by weight of biphenyl compound No. 5 in Table 1, 2 parts by weight of polycarbonate resin (Trademark "Panlite K-1300" made by Teijin Limited.) and 16 parts by weight of tetrahydrofuran were mixed to form a solution. This solution was coated on an aluminum-deposited polyester film by a doctor blade and then dried at 80° C. for 2 minutes and then at 120° C. for 5 minutes, so that a charge transport layer having a thickness of about 20 μm was formed on the aluminum-deposited polyester film.

A mixture of 13.5 parts by weight of bisazo pigment (P-2), 5.4 parts by weight of polyvinyl butyral (Trademark "XYHL" made by Union Carbide Japan K.K.), 680 parts by weight of tetrahydrofuran and 1020 parts by weight of ethyl cellosolve was dispersed and ground in a ball mill. To this dispersion, 1700 parts by weight of additional ethyl cellosolve was added to form a solution. This solution was coated on the above formed charge transport layer by spray coating and dried at 100° C. for 10 minutes, so that a charge generation layer having a thickness of about 0.2 μm was formed on the charge transport layer.

A methanol - n-butanol based solution of a polyamide resin (Trademark "CM-8000" made by Toray Silicone Co., Ltd.) was coated on the above formed charge generation layer by spray coating and dried at 120° C. for 30 minutes, so that a protective layer having a thickness of about 0.5 μm was formed on the charge generation layer. Thus, an electrophotographic photoconductor No. 19 according to the present invention was prepared.

Each of the thus prepared electrophotographic photoconductors No. 1 through No. 19 according to the present invention was charged negatively or positively in the dark under application of −6 kV or +6 kV of corona charge for 20 seconds, using a commercially available electrostatic copying sheet testing apparatus ("Paper Analyzer Model SP-428" made by Kawaguchi Electro Works Co., Ltd.). Then, each electrophotographic photoconductor was allowed to stand in the dark for 20 seconds without applying any charge thereto, and the surface potential Vpo (V) of the photoconductor was measured. Each photoconductor was then illuminated by a tungsten lamp in such a manner that the illuminance on the illuminated surface of the photoconductor was 4.5 lux, and the exposure $E_{1/2}$ (lux.-sec) required to reduce the initial surface potential Vpo (V) to ½ the initial surface potential Vpo (V) was measured. The results are shown in Table 3.

TABLE 3

| Photoconductor No. | Vpo (V) | $E_{1/2}$ (lux · sec) |
|---|---|---|
| 1 | −1185 | 0.95 |
| 2 | −1350 | 1.85 |
| 3 | −1200 | 1.20 |
| 4 | −1310 | 1.00 |
| 5 | −1340 | 2.80 |
| 6 | −1185 | 0.95 |
| 7 | −1230 | 1.03 |
| 8 | −970 | 2.70 |
| 9 | −1410 | 1.90 |
| 10 | −1130 | 1.35 |
| 11 | −1290 | 1.20 |
| 12 | −1100 | 1.10 |
| 13 | −1170 | 1.15 |
| 14 | −990 | 0.97 |
| 15 | −1410 | 1.02 |
| 16 | −1205 | 0.95 |
| 17 | −1070 | 2.15 |
| 18 | +1400 | 1.40 |
| 19 | +1230 | 0.94 |

Each of the above-mentioned electrophotographic photoconductors according to the present invention was incorporated in a commercially available electrophotographic copying machine and charged negatively or positively. Then it was exposed to the light through an original to form a latent electrostatic image on the surface of the photoconductor. The thus formed latent electrostatic image was developed by a dry-type developer to a visible image. The thus obtained visible image was transferred to a plain paper and fixed thereon, so that a clear transferred image was formed. In the case where a wet-type developer was employed, a clear image was formed likewise.

The electrophotographic photoconductors according to the present invention comprise a photoconductive layer comprising any of the above-mentioned specific biphenyl compounds serving as an organic photoconductive material, so that the resistance to heat and mechanical shocks of the photoconductor can be improved as well as the photoconductive properties thereof. Furthermore, the photoconductors according to the present invention can be manufactured at low cost.

What is claimed is:

1. An electrophotographic photoconductor comprising an electroconductive support and a photoconductive layer formed thereon comprising as an effective component at least one biphenyl compound represented by formula (I):

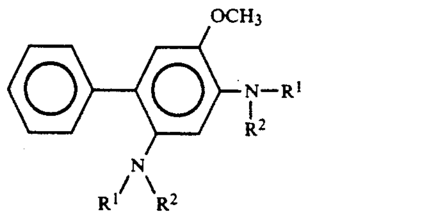

(I)

wherein $R^1$ and $R^2$ each is an alkyl group which may have a substituent, an alkoxyl group which may have a substituent, or an aryl group which may have a substituent, provided that at least one of $R^1$ and $R^2$ is an unsubstituted or substituted aryl group and a sensitizing dye.

2. The electrophotographic photoconductor as claimed in claim 1, wherein said alkyl group has 1 to 4 carbon atoms.

3. The electrophotographic photoconductor as claimed in claim 1, wherein said alkoxyl group has 1 to 4 carbon atoms.

4. The electrophotographic photoconductor as claimed in claim 1, wherein said aryl group is selected from the group consisting of

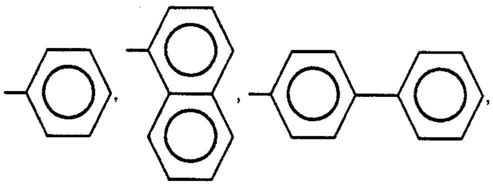

, and

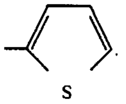

5. The electrophotographic photoconductor as claimed in claim 1, wherein said substituent of said alkyl group is a phenyl group.

6. The electrophotographic photoconductor as claimed in claim 1, wherein said substituent of said alkoxyl group is a phenyl group.

7. The electrophotographic photoconductor as claimed in claim 1, wherein said substituent of said aryl group is selected from the group consisting of an alkyl group having 1 to 4 carbon atoms and an alkoxyl group having 1 to 4 carbon atoms.

8. The electrophotographic photoconductor as claimed in claim 1, wherein both of $R^1$ and $R^2$ in the formula (I) are an unsubstituted or substituted aryl group.

9. The electrophotographic photoconductor as claimed in claim 1, wherein either $R^1$ or $R^2$ in the formula (I) is an unsubstituted or substituted aryl group, and the other is an unsubstituted or substituted alkyl group.

10. A charge transporting material having the formula (I):

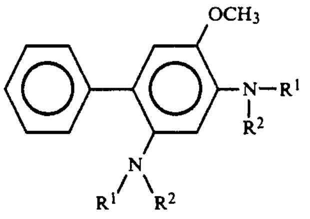

(I)

wherein $R^1$ and $R^2$ each is an alkyl group having 1 to 4 carbon atoms, which may have a substituent, an alkoxyl group having 1 to 4 carbon atoms, which may have a substituent, or an aryl group which may have a substituent, provided that at least one of $R^1$ and $R^2$ is an unsubstituted or substituted aryl group.

11. The charge transporting material as claimed in claim 10, wherein both of $R^1$ and $R^2$ in the formula (I) are an unsubstituted or substituted aryl group.

12. The charge transporting material as claimed in claim 10, wherein either $R^1$ or $R^2$ in the formula (I) is an unsubstituted or substituted aryl group, and the other represents an unsubstituted or substituted alkyl group.

13. A biphenyl compound having the formula (II):

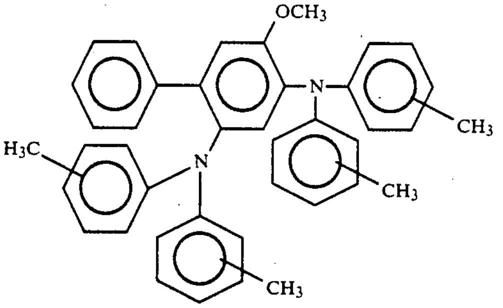

(II)

14. A biphenyl compound selected from the group consisting of:

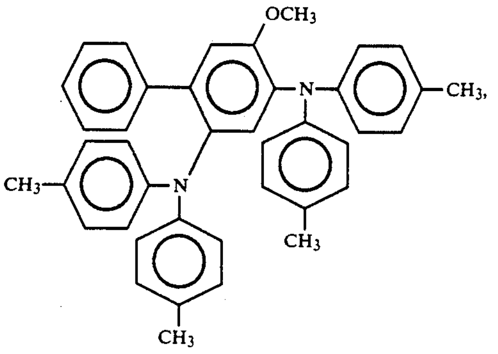

-continued
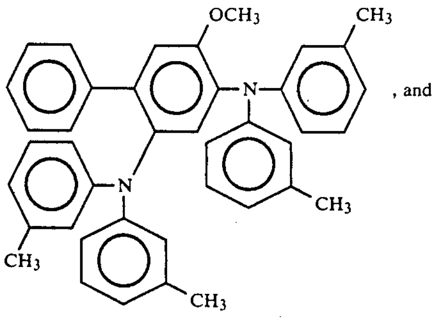
, and
-continued
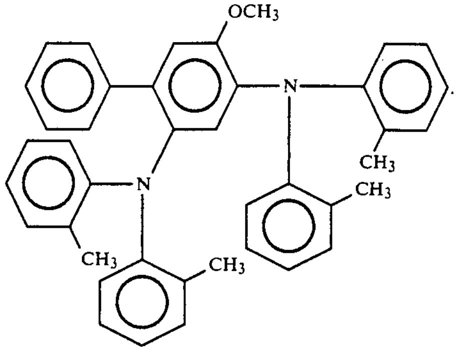
.
* * * * *

UNITED STATES PATENT AND TRADEMARK OFFICE

CERTIFICATE OF CORRECTION

PATENT NO. : 4,992,350

DATED : February 12, 1991

INVENTOR(S) : Masaomi SASAKI et al

It is certified that error appears in the above-identified patent and that said Letters Patent is hereby corrected as shown below:

In Column 2, line 12, "and considered" should read -- and are considered --;

line 24, "privide" should read -- provide --;

line 35, "charage" should read -- charge --.

In Column 9, line 13, "or 30 to 70" should read -- of 30 to 70 --;

line 43, "or 10 to 95" should read -- of 10 to 95 --.

Signed and Sealed this

Ninth Day of February, 1993

*Attest:*

STEPHEN G. KUNIN

*Attesting Officer*

*Acting Commissioner of Patents and Trademarks*